(12) United States Patent
Sugawara et al.

(10) Patent No.: US 7,468,174 B2
(45) Date of Patent: Dec. 23, 2008

(54) METHOD FOR PRODUCING CHLOROSULFONYL ISOCYANATE

(75) Inventors: Mutsumi Sugawara, Kurashiki (JP); Tsutomu Imagawa, Takaoka (JP); Fumitaka Masui, Takaoka (JP)

(73) Assignee: Nippon Soda Co., Ltd., Chiyoda-Ku, Tokyo (JP)

( * ) Notice: Subject to any disclaimer, the term of this patent is extended or adjusted under 35 U.S.C. 154(b) by 0 days.

(21) Appl. No.: 10/583,194

(22) PCT Filed: Dec. 15, 2004

(86) PCT No.: PCT/JP2004/019132

§ 371 (c)(1),
(2), (4) Date: Jun. 19, 2007

(87) PCT Pub. No.: WO2005/058806

PCT Pub. Date: Jun. 30, 2005

(65) Prior Publication Data

US 2007/0286789 A1    Dec. 13, 2007

(30) Foreign Application Priority Data

Dec. 16, 2003  (JP)  ............................. 2003-417611

(51) Int. Cl.
*C01B 21/084*  (2006.01)
*C01B 21/086*  (2006.01)

(52) U.S. Cl. ...................................... 423/365

(58) Field of Classification Search ................ 423/365, 423/366, 383, 384, 385, 386
See application file for complete search history.

(56) References Cited

U.S. PATENT DOCUMENTS 5,118,487 A    6/1992    Nakamura et al.

FOREIGN PATENT DOCUMENTS

| CH | 680292 A5 | 7/1992 |
| DE | 928896 | 6/1955 |
| EP | 0294613 B1 | 12/1988 |
| JP | 63-77855 | 4/1988 |
| JP | 01-228955 | 9/1989 |
| JP | 04-164063 | 6/1992 |
| JP | 2000-053630 | 2/2000 |
| JP | 2003-40854 | 2/2003 |
| JP | 2004-18500 | 1/2004 |

OTHER PUBLICATIONS

Graf, R. "Über die Umsetzung von Chlorcyan mit Schwefeltrioxyd" *Chem Ber*, 89:1071-79 (1956), partial.

*Primary Examiner*—Wayne Langel
*Assistant Examiner*—Brittany M Martinez
(74) *Attorney, Agent, or Firm*—Darby & Darby P.C.

(57) ABSTRACT

A method for producing chlorosulfonyl isocyanate by reaction of sulfur trioxide with cyanogen chloride, wherein chlorosulfonyl isocyanate or a solution including chlorosulfonyl isocyanate is used as a reaction solvent, sulfur trioxide and cyanogen chloride which are respectively diluted with the chlorosulfonyl isocyanate or the solution including chlorosulfonyl isocyanate are added at the same time to a reaction system in an almost equimolar amount under reflux. By the production method of present invention, chlorosulfonyl isocyanate can be produced from sulfur trioxide and cyanogen chloride in which the yield of the chlorosulfonyl isocyanate is high, the method has excellent operability, number of equipments is reduced, and time for controlling the temperature is saved.

2 Claims, No Drawings

METHOD FOR PRODUCING CHLOROSULFONYL ISOCYANATE

CROSS REFERENCE TO RELATED APPLICATIONS

This is a U.S. national phase application under 35 U.S.C. § 371 of International Patent Application No. PCT/JP2004/019132, filed Dec. 15, 2004 and claims the benefit of Japanese Application 2003-417611, filed Dec. 16, 2003. The International Application was published on Jun. 30, 2005 as International Publication No. WO 2005/058806 under PCT Article 21(2) the contents of which is incorporated herein in its entirety.

TECHNICAL FIELD

The present invention relates to a method for producing chlorosulfonyl isocyanate. More specifically, the present invention relates to a method for producing chlorosulfonyl isocyanate from sulfur trioxide and cyanogen chloride, in which the yield of the chlorosulfonyl isocyanate is high and the method has excellent operability.

BACKGROUND ART

Chlorosulfonyl isocyanate is industrially useful as an intermediate for producing pharmaceutical and agrochemical compounds, etc.

Conventionally, it is known that chlorosulfonyl isocyanate can be produced by the reaction of sulfur trioxide with cyanogen chloride, and several production methods thereof have been reported. For example, (a) Chem. Ber., 89, 1071 (1956) and West German Patent No. 928896 disclose a method in which sulfur trioxide is added to cyanogen chloride and reacted at a low temperature of −5° C. Also, (b) European Patent No. 294613 and Swiss Patent No. 680292A5 disclose a method for reacting sulfur trioxide with cyanogen chloride at 100 to 200° C.

However, the aforementioned method (a) is not preferable in view of cost. Moreover, there are problems with the quality, especially the purity, which does not meet commercial requirements. Furthermore, when the aforementioned method (b) is used, it is not easy to control the flow rate of sulfur trioxide and cyanogen chloride added to a reaction system, and the yield of the obtained chlorosulfonyl isocyanate is low and the quality thereof is poor, similar to when the method (a) is used.

In order to solve the aforementioned problems, (c) a method in which cyanogen chloride is added to sulfur trioxide and reacted while keeping the temperature of the reaction system at 20 to 50° C. (Japanese Unexamined Patent Application, First Publication No. S 63-77855), (d) a method in which sulfur trioxide and cyanogen chloride are added to a reaction system at the same time while keeping the temperature of the reaction system at 10 to 50° C. (Japanese Unexamined Patent Application, First Publication No. H1-228955), (e) a method in which sulfur trioxide and cyanogen chloride are reacted in a chlorinated hydrocarbon solvent (Japanese Unexamined Patent Application, First Publication No. H4-164063), and (f) a method in which cyanogen chloride is added to a mixture of sulfur trioxide and chlorosulfonyl isocyanate and reacted while keeping the temperature of the reaction system at −10 to 17° C. (Japanese Unexamined Patent Application, First Publication No. 2000-53630), and so forth have been proposed.

More recently, (g) a method has been proposed, in which a residue in a tank is decomposed after separating chlorosulfonyl isocyanate by distillation and, at the same time, a low-boiling-point fraction obtained by separating a chlorosulfonyl isocyanate by distillation or by decomposing/distilling the residue in the tank is recovered, and the recovered liquid is reused by adding when reacting sulfur trioxide and cyanogen chloride (Japanese Unexamined Patent Application, First Publication No. 2003-40854).

In those methods (c) to (g), chlorosulfonyl isocyanate having a comparably high yield (74 to 91%) and comparably high purity (90 to 98%) can be obtained by a comparably easy method.

However, in the methods (c) to (f), because a cooling operation is needed to maintain the temperature within a suitable temperature range in which the temperature may be raised due to an exothermic reaction with sulfur trioxide and cyanogen chloride and the cost for the cooling equipment is high, these methods are not satisfactory as an industrial method. Also, in order to improve the yield in those methods, it is essential to obtain chlorosulfonyl isocyanate by thermo-decomposing chloropyrosulfonyl isocyanate as a by-product. Because an operation in which chloropyrosulfonyl isocyanate is thermo-decomposed is dangerous, complex, and costly, these methods have industrial problems.

Moreover, in the method (f), the number of processes is large, and a complex after-treatment is needed for salvaging and reusing the low-boiling-point fraction, and thus the method (f) has a problem in that a lot of equipment is required.

In consideration of these circumstances surrounding the prior art, the object of the present invention is to provide a method for producing chlorosulfonyl isocyanate by a simple and easy operation, in which chlorosulfonyl isocyanate of high yield and high purity is obtained and the number of pieces of equipment is reduced.

BRIEF SUMMARY OF THE INVENTION

As a result of extensive studies to solve the aforementioned problems, the inventors of the present invention found that it becomes easy to control the flow rate of sulfur trioxide and cyanogen chloride added to a reaction system by diluting sulfur trioxide and cyanogen chloride with chlorosulfonyl isocyanate or a solution including chlorosulfonyl isocyanate. Also, the inventors of the present invention found that the reaction is completed at the same time as by-products are thermo-decomposed under reflux of solvent by using chlorosulfonyl isocyanate or a solution containing chlorosulfonyl isocyanate as the reaction solvent, thereby leading to completion of the present invention.

The present invention provides a method for producing chlorosulfonyl isocyanate by reaction of sulfur trioxide with cyanogen chloride, in which chlorosulfonyl isocyanate or a solution containing chlorosulfonyl isocyanate is used as the reaction solvent and sulfur trioxide and cyanogen chloride which are respectively diluted with chlorosulfonyl isocyanate or a solution containing chlorosulfonyl isocyanate are at the same time added to the reaction system under reflux in an almost equimolar amount.

A reflux temperature preferably to 50 to 110° C. in the method for producing chlorosulfonyl isocyanate of the present invention.

DETAILED DESCRIPTION OF THE INVENTION

The method for producing chlorosulfonyl isocyanate of the present invention is explained below in more detail.

The production method of the present invention is a method for producing chlorosulfonyl isocyanate by reaction of sulfur trioxide with cyanogen chloride.

(1) Sulfur Trioxide

Although the kind of sulfur trioxide used in the present invention is not especially limited provided that it is liquid, it is preferably a γ form because of high reactivity. Although the purity of sulfur trioxide used in the present invention is not especially limited, it is usually 90% by weight or more and preferable to 95% by weight or more. Also, the sulfur trioxide of the present invention may include a common polymerization inhibitor such as organosilicon, carbon tetrachloride, dimethyl sulfate, a boron compound, a phosphorus compound, and aromatic sulfonic acid. Although the content of the polymerization inhibitor is not especially limited, the content usually has a range within 0.001 to 1% by weight.

(2) Cyanogen Chloride

In the production method of the present invention, cyanogen chloride in the liquid state is used. Cyanogen chloride is industrially produced from hydrocyanic acid and chlorine, and is preferably dehydrated by dehydration or distillation. Also, although the purity of cyanogen chloride is not especially limited, the purity is usually 90% by weight or more and preferably 95% by weight or more.

Usage of cyanogen chloride (in the case of a continuous system, usage by the hour) is usually 0.8 to 1.2 molar equivalents, preferably to 0.9 to 1.1 molar equivalents, to sulfur trioxide. Usage of cyanogen chloride which is less than 0.8 molar equivalents or more than 1.2 molar equivalents is not preferable, because production of by-products such as chloropyrosulfonyl isocyanate or 2,6-dichloro-1,4,3,5-oxathiadiazine-4,4-dioxide increase producing detrimental effects such as a reduction of yield or prolongation of the reaction completion time.

(3) Method for Producing Chlorosulfonyl Isocyanate

In the production method of the present invention, chlorosulfonyl isocyanate or a solution containing chlorosulfonyl isocyanate is used as a reaction solvent and sulfur trioxide and cyanogen chloride which are respectively diluted with chlorosulfonyl isocyanate or solution including chlorosulfonyl isocyanate are at the same time added to the reaction system under reflux by an almost equimolar amount.

The purity of chlorosulfonyl isocyanate used as the reaction solvent and diluted solution of sulfur trioxide and cyanogen chloride is not especially limited. Chlorosulfonyl isocyanate having a high purity or a solution including chlorosulfonyl isocyanate may be used.

Examples of a solution including chlorosulfonyl isocyanate include, but are not limited to, a reaction liquid which is used when producing chlorosulfonyl isocyanate and a starting fraction, main fraction, and residue from a tank which are distillated when purifying by distillation. Also, a part of the reaction liquid may be left in the reaction tank as solvent for a following batch.

In the present invention, usage of chlorosulfonyl isocyanate or a solution including chlorosulfonyl isocyanate used as the reaction liquid is not especially limited provided that it is possible to control stirring and temperature. It is usually 0.2 to 1 molar equivalents, preferably to 0.2 to 0.5 molar equivalents, to the usage of sulfur trioxide.

In the present invention, sulfur trioxide and cyanogen chloride are diluted with chlorosulfonyl isocyanate or a solution including chlorosulfonyl isocyanate.

By using sulfur trioxide and cyanogen chloride which are diluted with chlorosulfonyl isocyanate or a solution including chlorosulfonyl isocyanate, the diluted solutions of cyanogen chloride and sulfur trioxide are added under reflux while controlling the flow rate. Therefore, the production of by-products can be prevented and chlorosulfonyl isocyanate can be selectively obtained.

Usage of sulfur trioxide and cyanogen chloride diluted with chlorosulfonyl isocyanate or a solution including chlorosulfonyl isocyanate is not especially limited when sulfur trioxide is diluted. When cyanogen chloride is diluted, a sufficient usage amount is that which does not cause cyanogen chloride to volatilize from chlorosulfonyl isocyanate as diluted solution. It is usually 0.2 to 1 molar equivalents, preferably to 0.2 to 0.5 molar equivalents, to the usage of cyanogen chloride.

A method for adding sulfur trioxide diluted with chlorosulfonyl isocyanate or a solution including chlorosulfonyl isocyanate and cyanogen chloride diluted with chlorosulfonyl isocyanate or a solution including chlorosulfonyl isocyanate (hereinafter, they may be referred to as "raw material") include a batch system and continuous system. In the case of a continuous system, a tank for completing the reaction may be provided in addition to a reaction tank.

In the production method of the present invention, sulfur trioxide and cyanogen chloride which are respectively diluted with chlorosulfonyl isocyanate or solution containing chlorosulfonyl isocyanate are added at the same time to the reaction system under reflux in an almost equimolar amount. The term in "by an almost equimolar amount" in the description means that the charge ratio of sulfur trioxide to cyanogen chloride is from 0.8:1.2 to 1.2:0.8, preferably to 1.1:0.9 to 0.9:1.1, by molar ratio. The charge ratio means an amount per hour, in the case of a continuous system.

When a balance of the charge amount of the raw material is lost, the production of by-products such as chloropyrosulfonyl isocyanate or 2,6-dichloro-1,4,3,5-oxathiadiazine-4,4-dioxide increases producing detrimental effects such as a reduction of yield or prolongation of the reaction completion time.

A charge temperature and a reaction temperature of the raw material indicate a reflux temperature of chlorosulfonyl isocyanate or a solution including chlorosulfonyl isocyanate as the solvent.

The reflux temperature is usually 50 to 110° C. In consideration of the decomposition of chloropyrosulfonyl isocyanate or 2,6-dichloro-1,4,3,5-oxathiadiazine-4,4-dioxide etc. for a short time, the reflux temperature is preferable to 100 to 110° C. In the case of using chlorosulfonyl isocyanate as the reaction solvent within the above reflux temperature range, cooling equipment is not needed and by-products including chloropyrosulfonyl isocyanate can be thermo-decomposed at the same time.

A charge time for the raw material of the present invention is not especially limited provided that the condenser is allowed complete the reaction. In the case of using a batch system, the charge time is usually 0.25 to 2.5 hours. In the case of using a continuous system, the reaction may be performed by charging the amount of raw material according to the treatment capability of the equipment.

In the production method of the present invention, it is preferable to provide a sufficient reaction time in order to produce chlorosulfonyl isocyanate having an excellent yield as the objective product and decompose by-products completely. The reaction time for the raw material to be sufficiently consumed and by-products to be decomposed is usually 0.5 to 15 hours, preferably 5 to 10 hours.

(4) Operation of After-treatment

After the reaction, chlorosulfonyl isocyanate as the objective product can be isolated by refinement of the reaction liquid. The refinement of the reaction liquid after completing the reaction is usually performed using a normal distillation column under normal pressures or reduced pressure. Distillation conditions such as pressure, temperature, number of stages, or number of times are not especially limited. In the case of a continuous system, the reaction liquid is continuously ejected from the tank to complete the reaction and continuously distillated, and thus chlorosulfonyl isocyanate as the objective product can be isolated.

The present invention will be explained below in more detail by reference to the following Examples and Comparative Example, but the invention should not be construed as being limited thereto.

EXAMPLE 1

14.3 g (0.1 mol) of chlorosulfonyl isocyanate was placed in a 100 ml-four-neck flask with a condenser and the temperature thereof was raised to the reflux temperature while stirring. To this solution, a mixed solution of 40.4 g (0.5 mol) of sulfur trioxide and 14.2 g (0.1 mol) of chlorosulfonyl isocyanate and a mixed solution of 30.9 g (0.5 mol) of cyanogen chloride and 14.2 g (0.1 mol) of chlorosulfonyl isocyanate were added dropwise at the same time in the same molar equivalents for 15 minutes under reflux to obtain a reaction liquid. Then, the reaction liquid was stirred for 9.5 hours at the reflux temperature (from 104 to 108° C.). The yield of chlorosulfonyl isocyanate was 90% after completing the reaction, in which the used sulfur trioxide was based on and the amount of chlorosulfonyl isocyanate used as reaction solvent and solution for diluting the raw material was removed. Then, simple distillation was performed under normal pressures to obtain 94.1 g (the purity of 99%) of chlorosulfonyl isocyanate as the fraction by boiling at 106 to 108° C. under 1.013 kPa.

EXAMPLE 2

14.3 g (0.1 mol) of chlorosulfonyl isocyanate was placed in a 100 ml-four-neck flask with a condenser and the temperature thereof was raised to the reflux temperature while stirring. To this solution, a mixed solution of 40.6 g (0.5 mol) of sulfur trioxide and 14.3 g (0.1 mol) of chlorosulfonyl isocyanate and a mixed solution of 31.4 g (0.5 mol) of cyanogen chloride and 28.4 g (0.2 mol) of chlorosulfonyl isocyanate were added dropwise at the same time in the same molar equivalents for 20 minutes under reflux to obtain a reaction liquid. Then, the reaction liquid was stirred for 9 hours at the reflux temperature (from 103 to 108° C.). The yield of chlorosulfonyl isocyanate was 89% after completing the reaction, in which the used sulfur trioxide was based on and the amount of chlorosulfonyl isocyanate used as reaction solvent and solution for diluting the raw material was removed. Then, simple distillation was performed under normal pressures to obtain 108.5 g (the purity of 99%) of chlorosulfonyl isocyanate as the fraction by boiling at 106 to 108° C. under 1.013 kPa.

COMPARATIVE EXAMPLE 14.3 g (0.1 mol) of chlorosulfonyl isocyanate was placed in a 100 ml-four-neck flask with a condenser and the temperature thereof was raised to the reflux temperature while stirring. To this solution, a mixed solution of 40.2 g (0.5 mol) of sulfur trioxide and 30.8 g (0.5 mol) of cyanogen chloride were added dropwise at the same time in the same molar equivalents for 60 minutes under reflux to obtain a reaction liquid. In this operation, cyanogen chloride in the liquid was vaporized, passed through a flow meter, and added dropwise to the reaction system by another condenser, but the flow rate of cyanogen chloride was not fixed. Then, the reaction liquid was stirred for 9 hours at the reflux temperature of the reaction liquid which was gradually raised from 95 to 109° C. At this point, the yield of chlorosulfonyl isocyanate was 67%, in which the used sulfur trioxide was based on and the amount of chlorosulfonyl isocyanate used as reaction solvent and solution for diluting the raw material was removed.

INDUSTRIAL APPLICABILITY

By the production method of present invention, chlorosulfonyl isocyanate can be produced from sulfur trioxide and cyanogen chloride in which the yield of the chlorosulfonyl isocyanate is high, the method has excellent operability, the amount of equipment is reduced, and time for controlling the temperature is saved.

What is claimed is:

1. A method for producing chlorosulfonyl isocyanate by reaction of sulfur trioxide with cyanogen chloride, wherein
chlorosulfonyl isocyanate or a solution including chlorosulfonyl isocyanate is used as a reaction solvent; and
sulfur trioxide and cyanogen chloride which are respectively diluted with the chlorosulfonyl isocyanate or the solution including chlorosulfonyl isocyanate are added at the same time to a reaction system in a charge ratio of sulfur trioxide to cyanogen chloride from 0.8:1.2 to 1.2:0.8, by molar ratio, under reflux.

2. A method for producing chlorosulfonyl isocyanate according to claim 1, wherein a reflux temperature is from 50 to 110° C.

* * * * *